United States Patent
Carney et al.

(10) Patent No.: US 7,433,732 B1
(45) Date of Patent: Oct. 7, 2008

(54) REAL-TIME BRAIN MONITORING SYSTEM

(75) Inventors: Paul R. Carney, Gainesville, FL (US); J. Chris Sackellares, Gainesville, FL (US); Deng S. Shiau, Gainesville, FL (US)

(73) Assignee: University of Florida Research Foundation, Inc., Gainesville, FL (US)

( * ) Notice: Subject to any disclaimer, the term of this patent is extended or adjusted under 35 U.S.C. 154(b) by 176 days.

(21) Appl. No.: 11/065,703

(22) Filed: Feb. 25, 2005

Related U.S. Application Data (60) Provisional application No. 60/547,413, filed on Feb. 25, 2004.

(51) Int. Cl.
A61B 5/00 (2006.01)

(52) U.S. Cl. ..................................... 600/544

(58) Field of Classification Search ................. 600/300, 600/301, 544, 545
See application file for complete search history.

(56) References Cited

U.S. PATENT DOCUMENTS

| | | | |
|---|---|---|---|
| 5,458,117 A * | 10/1995 | Chamoun et al. | 600/547 |
| 5,769,793 A * | 6/1998 | Pincus et al. | 600/515 |
| 6,304,775 B1 | 10/2001 | Iasemidis et al. | |
| 6,931,274 B2 * | 8/2005 | Williams | 600/544 |
| 2002/0103512 A1 | 8/2002 | Echauz et al. | |
| 2003/0013981 A1 * | 1/2003 | Gevins et al. | 600/544 |
| 2004/0122335 A1 | 6/2004 | Sackellares et al. | |
| 2004/0127810 A1 | 7/2004 | Sackellares et al. | |

OTHER PUBLICATIONS

Albano AM, Bedonie C, Cellucci CJ, Miller V, Ree J, Torrueia A, Harner RN, Rapp PE. Spatiotemporal EEG Information transfer in an episode of epilepsy. In: *Nonlinear Dynamics and Brain Functioning*. Eds: Pradhan J, Sreeivansan R, Rapp PE. Nova Science Pub: NY, 1999.

Andre M. Matisse N, Vert P., Debruille C. Neonatal seizures: recent aspects. Neuropediatrics. 19:201-207, 1988.

Bye Ame and Flanagan D. Spatial and temporal characteristics of neonatal seizures. Epilepsia, 36(10):1009-1016, 1995.

Bye Ame, Cunningham CA, Chee KY, Flanagan D. Outcome of neonates with electrographically identified seizures, or at risk of seizures. Pediatr neurol. 16:225-231, 1997.

(Continued)

*Primary Examiner*—Robert L Nasser
(74) *Attorney, Agent, or Firm*—Alston & Bird LLP (57) ABSTRACT

An exemplary method for monitoring neonate brain function includes processing electroencephalographic data of the neonate to calculate at least one measure, the at least one measure including a non-linear measure, comparing the calculated at least one measure against at least one baseline threshold, wherein the at least one baseline threshold corresponds to a neonate age range, and outputting a result of the comparison. An exemplary system for monitoring neonate brain function includes a computing device for processing electroencephalographic data of the neonate to calculate at least one measure, the at least one measure including a non-linear measure, and for comparing the calculated at least one measure against at least one baseline threshold, wherein the at least one baseline threshold corresponds to a neonate age range, and a display for displaying a result of the comparison.

16 Claims, 2 Drawing Sheets

OTHER PUBLICATIONS

Bullock TH McClune MC, Achimowicz JZ, Iragui-Madoz VJ, Duckrow RB, Spencer SS. EEG coherence has structure in the millimeter domain: Subdural and hippocampal recordings from epileptic patients. Electroencephalo Clin Neurophysio, 95:161-177, 1995.

Celka P, Boashash B, Colditz, P. Brain storming; digital processing of EEG signals improves classification, prediction, and monitoring, Eds: Colditz PB, Burke CJ, Celka P., IEEE Engineering in Medicine and Biology., 20 (5); 2001.

Clancy R. Interictal sharp EEG transients in neonatal seizures. J. Child Neurol., 4:30-38, 1989.

Clancy RR and Legido A. The exact ictal and interictal duration of electroencephalographic neonatal seizures. Epilepsia, 28:537-541, 1987b.

Clancy RR and Legido A. Postnatal epilepsy after EEG-confirmed neonatal seizures, Epilepsia, 32:69-76, 1991.

Collins RC, Olney JW, Lothman EW. Metabolic and pathological consequences of focal seizures. In: Epilepsy. Eds: Ward AA, Penry JK, Purpura D. 1983.

Dreyfus-Brisac C, Monod N. Electroclinical studies of status epilepticus and convulsions in the newborn. In: Neurological and Electroencephalographic Correlative Studies in Infancy. Eds: Kellaway P, Petersen I, New York: Grune and Statton; 250-272, 1964.

Duckrow RB and Spencer SS. Regional coherence and the transfer of ictal activity during seizure onset in the medial temporal lobe. Electroencephal Clin Neurophysio, 414-422, 1982.

Ellenberg JH, Hirtz DG, Nelson KB. Age at onset of seizures in young children. Ann Neurol, 15:172-134, 1984.

Ellison PH, Largent JA. A scoring system to predict outcome following neonatal seizures. J Pediatr, 99:455-459, 1981.

Engoren M. Approximate entropy of respiratory rate and tidal volume during weaning from mechanical ventilation. Crit Care Med, 26:2046-2056, 1998.

Fenichel GM. Neonatal Neurology. 2nd Ed., New York: Churchill-Livingstone; 1985.

Gotman J. Automatic recognition of epileptic seizure in the EEG. Electroenceph. Clin. Neurophysiol. 54:30-540, 1982.

Gotman J. Measurement of small time differences between EEEG channels: methods and application to epileptic seizure propagation. Electro Clinic Neurophys, 56:501-514, 1983.

Gotman J. Automatic seizure detection: improvements and evaluation. Electroenceph Clin Neurophysiol., 76: 317-324, 1990.

Gotman J, Flanagan D, Zhang J, Rosenblatt B. Automatic seizure detection in the newborn: methods and initial evaluation. Electroenceph Clin Neurophysiol.. 103: 356-362, 1997a.

Gotman J, and Levtova V. Amygdala-Hippocampus Relationships in Temporal Lobe Seizures: A Phase-Coherence Study. Epilepsy Research. Epilepsy Research. 25:51-57, 1996.

Gotman J, Flanagan D, Rosenblatt B, Bye A, Mizrahi EM. Evaluation of an automatic seizure detection method for the newborn EEG. Electroenceph Clin Neurophysiol., 103: 363-369, 1997b.

Holden KR, Melilts ED, Freeman JM. Neonatal seizures. I. Correlation of prenatal and perinatal events with outcomes. Pediatrics, 70:165-176, 1982.

Holmes GL, Chronopoulos A, Stafstrom CE. Effects of kindling on subsequent learning, memory, behavior, and seizures susceptibility. Brain Res Dev Brain Res. 73: 71-77, 1993a.

Hoirnes GL, Khazipov R, Ben-Ari Y. New concepts in neontal seizures. NeuroReport. 13(1):A3-A8, 2002.

Hrachovy RA, Mizrahi EM, Kellaway P. Electroencephalography of the newborn. Eds: Daly D, Pedley TA. In: *Current Practice of Clinical Electroencephalography.* 2nd ed. New York: Raven; 201-242, 1990.

Iasernidis LD, Sackellares JC, Zarari HP, Williams WJ. Phase space topography and the Lyapunov exponent of electrocorticograms in partial seizures. Brain Topography, 2(3) 1-18, 1990.

Iasemidis LD, Pardalos PM, Sackellares JC, Shiau DS. "Quadratic Binary Programming and Dynamical System Approach to Determine the Predictability of Epileptic Seizures." *Journal of Combinatorial Optimization* 5(1), 9-26, 2001.

Iasemidis LD, Shiau DS; Chaowolitwongse W., Prasad A, Veeramani B, Sackellares JC, Pardalos PM, Carney PR, and Tsakalis K. Adaptive Epileptic Seizure Prediction System. IEEE Transactions in Biomedical Engineering, in press.

Iasemidis LD, Pardalos PM, Shiau DS, Chaowolitwongse W., Narayanan K, Kumar S, Carney PR, Sackellares JC. Prediction of human epileptic seizures based on optimization and phase changes of brain electrical activity. Optimization Methods and Software, in press.

Jenkins GM and Watts DG. *Spectral Analysis and its Applications.* Holden-Day SF, 2968.

Jensen FE, Applegate CD, Holtzman D. Epileptogenic effect of hypoxia in the immature rodent brain. Ann Neurol. 29:629-637, 1991.

Kaiser JF. On a simple algorithm to calculate the "energy" of a signal. In: Proceedings of ICASSP, 381-384, 1990.

Koopmans LH. *The Spectral Analysis of Time Series.* San Diego, CA: Academic press, 1995.

Lehnertz K and Eiger C. Can epileptic seizures be predicted? Evidence from nonlinear time series analysis of brain electrical activity. Phys Rev Lett., 80: 5019-5022, 1998.

Litt B, Esteller R, Echauz J, D'Alessandro M, Shor R, Henry T, Pennell P, Epstein C, Bakay R, Dichter M, Vachtsevanos G. Epileptic seizures may begin hours in advance of clinical onset: A report of five patients. Neuron., 30(1):51-64, 2001.

Lombroso CT. Neonatal EEG polygraphy in normal and abnormal newborns. In: *Electroencephalography. Basic Principles, Clinical Applications and Related Fields.* Eds: E.Neiderrneyer and FH Lopes da Silva. Baltimore, MD, Wiliams and Wilkins, 802-875:1993.

Lowenstein DH, Shimosaka S, So YT. The relationship between electrographic seizure activity and neuronal injury. Epilepsy Res. 10:49-54, 1991.

Lui A, Hahn JS, Heldt GP, Coen RW. Detection of neonatal seizures through computerized EEG analysis. Electroenceph Clin Neurophysiol., 82: 30-37, 1992.

Mars NJI and Lopes Da Silva FH. EEG analysis methods based on information theory. In: *Methods of Analysis of Brain Electrical and Magnetic Signals.* EEG Handbook (revised series, vol. 1), AS Gevins and A. Remand, Eds, Elsevier:Amsterdam, 297-307, 1987.

Martinerie J, Adam C, Le Van Quyen M, Baulac M, Clemenceau S, Renault B, Varela FJ. Epileptic seizures can be anticipated by nonlinear analysis. Nature Medicine., 4(10): - 1173-1176, 1998.

Meldrum B. Physiological changes during prolonged seizures and epileptic brain damage. Neuropadiatrie, 9:203-212, 1978.

Mizrahi EM, Kellaway P. Characterization of seizures in neonates and young infants by time-synchronized electroencephalographic/polygraphic/video monitoring. Ann Neurol, 16:383, 1984a.

Mizrahi EM, Kellaway P. Characterization and classification of neonatal seizures, Neurology, 37:1837-1855, 1987.

Mizhahi EM, Kellaway P. *Diagnosis and Management of Neonatal Seizures.* Lippencott-Raven, Philadel., 1st ed., 1998.

Morrison S and Newell KM. Inter- and intra-limb coordination in arm tremor. Exp Brain Res, 110:455-464, 1996.

Ortibus EL, Sum JM, Hahn JS. Predictive value of EEG for outcome and epilepsy following neonatal seizures. Electroencephalogr Clin Neurophysiol. 98:175-185, 1996.

Pincus SM. Approximate entropy (ApEn) as a complexity measure. Chaos, 5:110-117, 1995.

Pincus SM, and Huang WM. Approximate entropy-statistical properties and applications. Communications in Statistics Theory and Methods, 21(11):3061-3077, 1991.

Pincus SM and Singer BH. Randomness and degrees of irregularity. PNAS, 93:2083-2088, 1996.

Osorio I, Frei, MG, Giftakis J, Peters T, Ingram J, Turnbull M, Herzog M, Rise MT, Schaffner S, Wennberg RA, Walcak TS, Risinger MW, Ajomone-Marsan C. Performance reassessment of a real-time seizure-detection algorithm on long ECoG series. Epilepsia. 43(12):1522-35, 2002.

Otnes RK and Enochson L. Digital Time Series Analysis, New York: John Wiley and Sons, 1972.

Rogowski ZI, Gath I, Bental E. On the prediction of epileptic seizures. Biological Cybernetics., 42: 9-15, 1981.

Rose AL, Lombroso CT. A study of clinical, pathological, and electroencephalographic features in 137 full-term babies with a long-term follow-up [or is it Neonatal seizure states]. Pediatrics, 45:404-425, 1970.

Rowe JC, Holmes GL, Hafford J. Prognostic value of the electroencephalogram in term and preterm infants following neonatal seizures. Electroencephalogr Clin neurophysio, 60: 183-196, 1985.

Sackellares JC, Lasemidis LD, Gilmore RL, Roper SN. Epilepsy-when chaos fails. In: *Chaos in the brain?* Eds: Lehnertz K, Arnhold J, Grassberger P, Eiger CE. Singapore: World Scientific, 2000.

Schmitz O, Porksen N, Nyholm B, Skjaerbaek C, Butler PC, Veldhuis JD, Pincus SM. Disorderly and nonstationary insulin secretion in relatives of patients with NIDDM. Am J Phys, 272:E218-26, 1997.

Scher MS, Hamid MY, Steppe DA, Beggarly ME, Painter MJ. Ictal and interictal electrographic seizure durations in preterm and term neonates. Epilepsia, 34:284-288, 1993.

Scher MS, Aso K, Beggarly ME, Hamid MY, Steppe DA, Painter MJ. Electrographic seizures in preterm and full-term neonates: clinical correlates, associated brain lesions, and risk for neurologic sequelae. Pediatrics, 91:128-134, 1993.

Scher MS, Sun M, Steppe DA, Guthrie RD, Sclabassi RJ. Comparison of EEG spectral and correlation measures between healthy term and preterm infants. Prediatr Neural., 10: 104-108, 1994.

Shannon CE and Weaver W. *The Mathematical Theory of Communication*. Urbana, University of Illinois Press, 1949.

Statstrom CE, Holmes GL, Chronopoulos A, Thurber S, Thompson JL. Age-dependent cognitive and behavior deficits following kainic acid-induced seizures. Epilepsia 34:420432, 1993.

Stockard-Pope JE, Werner SS, Bickford RG. *Atlas of Neonatal Electroencephalography*, Second ed. New York, NY: Raven, 1992.

Volpe JJ. Neonatal seizures. In: *Neurology of the Newborn*. Philadelphia:WB Saunders; 172-207, 1995.

Wasterlain CG. Neonatal seizures and brain growth. Neuropadiatrie, 9:213-228, 1978.

Zaveri HP, Williams WJ, Sackellares JC. Energy based detection of seizures. In: Proceedings of the Annual International Conference of the IEEE Engineering in Medicine and Biology Society, IEEE, 1993.

Zaveri HP, Williams WJ, Sackellares JC, Beydoun A, Duckrow RB, Spencer SS. Measuring the coherence of intracranial electroencephalograms. Clin Neurophys, 110:1717-1725, 1999.

Zaveri HP, Duckrow RB, Spence SS. The effect of a scalp reference signal on coherence measurements of intracranial electroencephalograms. Clin Neurophys, 111(7)1293-1299, 2000.

* cited by examiner

REAL-TIME BRAIN MONITORING SYSTEM

This application claims priority the benefit of U.S. Provisional Application No. 60/547,413 filed in the U.S. Patent and Trademark Office on 25 Feb. 2004. U.S. Provisional Application No. 60/547,413 is hereby incorporated by reference in its entirety.

BACKGROUND OF THE INVENTION

Neonatal seizures may be the most frequent, and often the only clinical sign of central nervous system dysfunction in newborn children. Such events can be difficult to identify clinically. Seizures raise immediate concerns about the underlying cause of brain disorder, associated clinical conditions, the effect seizures may have on the developing brain, the need for antiepileptic drugs, and the effect antiepileptic drugs may have on the newborn child. In preterm infants, the immature brain is resistant to acute-induced cell loss, but there are functional abnormalities following seizure with impairment in visual-spatial memory and reduced threshold. Neonatal seizures are also associated with many activity-dependent changes in brain development including altered synaptogenesis and reduction in neurogenesis. However, the inherent difficulty in recognizing seizures may limit the effectiveness of the clinician in the care of infant children, particularly those suffering seizures. In addition, because of the developmental immaturity of the brain, neonatal seizures may have unique clinical manifestations when compared to seizures in older infants, children, and adults. Seizures may be brief and infrequent and may also occur when trained personnel are not observing infants. Thus, the clinician may be left to rely on historical information that may be incomplete or inaccurate. As a result, neonatal seizures may be more difficult to recognize than those of older age groups. Further, seizures in this age group may not occur until several days after an insult, and some newborns are pharmacologically paralyzed to improve ventilation, thus making visual identification of seizure behavior impossible.

The sequelae of seizures during the newborn period can be significant, including for example death, abnormal neurologic findings, mental retardation, brain growth retardation, and development of postnatal epilepsy. Methods of multivariant analysis have been proposed to predict the ultimate outcome of newborns that have experienced seizures during the newborn period. Such methods include consideration of interictal electroencephalogram (EEG) features from one recording or from serial recordings, the ictal EEG, neurological examination at the time of seizure, character or duration of seizure, etiology, findings on neuroimaging, conceptional age (i.e. a child's age as measured from the date of conception), and birth weight.

In clinical practice, predicting outcome in the acute period is most reliably based on assessment of an initial degree of brain injury and persistence of brain dysfunction during the ensuing first few days. The EEG has an important role in the diagnosis and management of neurological disorders in newborns, and in at least one study was proven superior to clinical examination of newborns for early detection and prognosis of brain dysfunction. The EEG can also provide an important measure of quality of brain function in critically ill infants. Continuous video-EEG monitoring of critically ill children can provide information about the presence of seizures, and can be useful to monitor a child's response to anti-convulsant treatment. Further, EEG monitoring can be used to provide "real time" and continuous information concerning brain function, in contrast to other techniques such as head ultrasonography and neuroimaging studies which assess brain structure. EEG may identify pathological changes in brain function and provide prognostic markers, which can be useful to monitor response to therapy and aid clinical management, for example to determine duration of therapy. Sensitive and specific EEG measures can provide relevant information about brain function prior to clinical manifestation, which may present a window of opportunity for appropriate interventions. Monitoring can be used to determine whether the newborn is experiencing state changes in EEG, capturing a clinical seizure on video that is closely correlated with EEG seizure activity is a definite criterion for the monitoring-based diagnosis of a seizure of epileptic origin. However, identifying EEG seizures can be a challenging experience, even for the more experienced clinical neurophysiologist. Also, video-EEGs are often reviewed post-hoc, often several hours after a seizure actually occurred. In many neonatal intensive care units (ICUs), "real-time" interpretation of the EEG is not possible or practical, and few neonatal health care professionals have received sufficient training in neonatal EEG interpretation to assist with "real-time" EEG analysis at the bedside.

An ability to monitor brain function and dysfunction, and detect neonatal seizures in "real-time", would greatly empower the clinician's ability to make timely and accurate medical decisions about the status of a newborn child's brain. An ability to identify a newborn at risk for brain problems in the acute setting and in real time through quantitative means, would provide a greater degree of control over this disorder so that clinicians can make more efficient and effective treatment and management decisions. Furthermore, quantitative identification of brain vulnerable states also offers the scientist better tools in formulating an understanding of the disorder. Validated quantitative measures of EEG activity may help to determine the degree of brain dysfunction, which in turn may provide some early clinical insight into long-term outcome.

The major new thrust of research work in EEG analysis is to extract information from EEGs, which is not available by visual analysis of the raw recording. More recently, the ongoing technical revolution in computer storage and processing power has allowed greater ability to collect and analyze comprehensive data sets. By quantitatively examining EEG data in adult patients with epilepsy, measurable sub-threshold changes that precede and accompany seizures have been reported. In particular, it has been suggested that brain electrical activity evolves to a measurable linear or nonlinear state of maximum order just prior to, and during seizure onset. Automatic seizure detection methods have been applied to newborns by using three types of analysis, including spectral analysis, spike detection, and low-pass digital filtering. Initial evaluation indicated that more than 70 percent of seizures, and almost 80 percent of seizure clusters, were detected with a false detection rate of 1.7 per hour. In the testing of data set, the method was validated using a completely new set of data from 54 patients, and the average detection rate was nearly 70 percent with a false detections rate of 2.3 per hour (Gotman et al., EEG and Clinical Neurophysiology, 103(3): 356-369, 1997).

These results suggest that there is potential for reliable automated seizure detection methods after the suspected insult.

SUMMARY

An exemplary method for monitoring neonate brain function includes processing electroencephalographic data of the neonate to calculate at least one measure, the at least one measure including a non-linear measure, comparing the calculated at least one measure against at least one baseline threshold, wherein the at least one baseline threshold corresponds to a neonate age range, and outputting a result of the comparison. An exemplary system for monitoring neonate brain function includes a computing device for processing electroencephalographic data of the neonate to calculate at least one measure, the at least one measure including a non-linear measure, and for comparing the calculated at least one measure against at least one baseline threshold, wherein the at least one baseline threshold corresponds to a neonate age range, and a display for displaying a result of the comparison.

BRIEF DESCRIPTION OF THE DRAWING FIGURES

The accompanying drawings provide visual representations which will be used to more fully describe the representative embodiments disclosed herein and can be used by those skilled in the art to better understand them and their inherent advantages. In these drawings, like reference numerals identify corresponding elements.

DETAILED DESCRIPTION OF THE INVENTION

Figure 1:
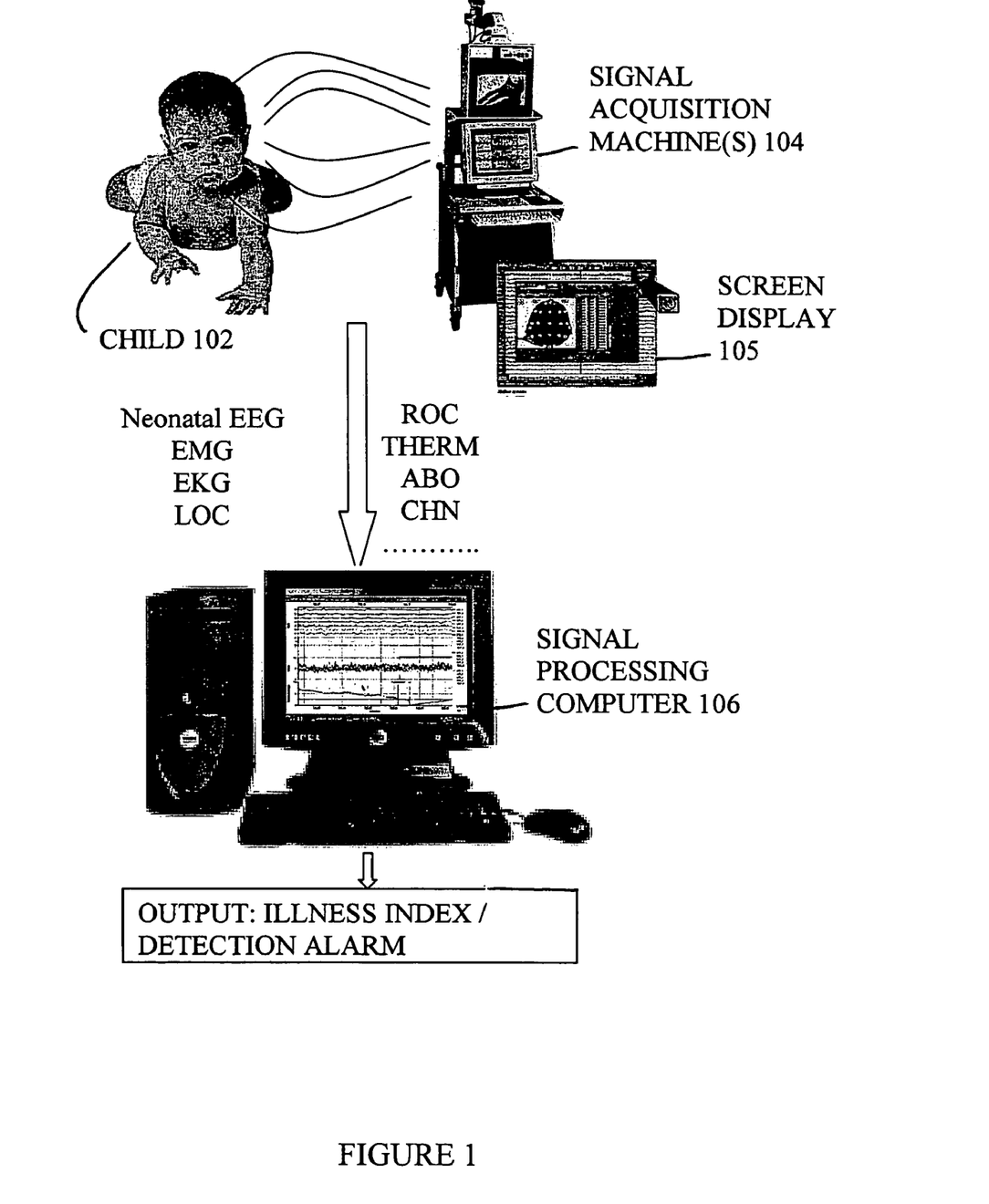
FIG. 1 illustrates an exemplary neonatal medical monitoring device.

FIG. 1 illustrates an exemplary neonatal medical monitoring device, wherein a child 102 is monitored by a signal acquisition machine 104. Signals monitored or acquired include electroencephalographic (EEG) data (including for example left oculocephalic channels (LOC) and right oculocephalic channels (ROC)), temperature (e.g. from a nasal thermistor), heart rate, oxygen saturation (e.g. pulse oximetry), electromyogram (EMG) data, electrocardiogram (EKG), level of consciousness, abdominal channel (ABO) data, chin electrode (CHM) data, and so forth. The signal acquisition machine 104 can include a display, for example that displays the captured data and/or other information, as shown in the exemplary screen display 105. Captured data is transferred from the signal acquisition machine 104 to signal processing computer 106, which evaluates the data and outputs an illness index and/or an alarm signal(s) based on the evaluation. The alarm can be visual (e.g. featured on a display of the machine 104, the computer 106, and/or other display), aural, or any sort, variety, form or combination of signal(s) that convey information. The signal processing computer 106 can be central or distributed in nature, and communication link(s) between the computer system 106 and the signal acquisition machine 104 can be wired, wireless, or any other method or mechanism capable of conveying the data. Those skilled in the art will recognize that the signal processing computer 106 and the signal acquisition machine 104 can be consolidated into one machine or location, for example a single computer handling both signal acquisition and processing.

The overall system shown in FIG. 1 can be used consistent with exemplary embodiments of the invention to capture a child's vital signs including EEG, process the EEG using various measures, and then compare the processed results against baseline values or thresholds with respect to normal and abnormal brain function or behavior children in the child's same age group. Based on the comparison, detection or identification of seizures or other abnormal brain function can be performed on a real time basis in for example a clinical setting, and an alarm or alert can be provided to the health care professional on duty in the event that abnormalities requiring attention are detected. Other data regarding the child's condition (pulse oximetry readings, pulse rate, etc.) can be evaluated in conjunction with the EEG data to provide a more accurate evaluation of the child's brain function and/or provide information that can be used in an automated fashion or by the health care professional to determine causation of abnormal brain function and thus aid in diagnosis or therapy. The system can be integrated into an overall automated monitoring system that tracks, evaluates, and reports on all important or critical aspects of the child's health or physical condition. The system can also be used to gather research data, for example data samples from multiple patients, and to statistically evaluate sample data to help determine or refine estimates of or parameters delimiting normal and abnormal brain function of children, in particular neonates, within different age groups or development levels.

In an exemplary embodiment, the signal processing computer 106 processes captured signals in real-time, and applies blind source separate (BSS) algorithms to reduce noise in the signals. Signal processing performed by the computer 106 includes, for example, calculation of both linear and nonlinear measures including 1) signal energy, 2) approximate entropy (ApEn), 3) short-term maximum Lyapunov exponent (STLmax or $STL_{max}$), 4) cross-ApEn, 5) coherence, 6) mutual information, 7) pattern-match ApEn and/or pattern-match regularity statistics, 8) time-frequency distributions (TFDs), and 9) bi-spectrum index. Methods 1-3 and 6-9 are linear and nonlinear univariate, while methods 4-5 are bivariate. We employ univariate measures to characterize the behavior of a single signal in the system, and bivariate measures to study the relationship between signals within the brain network. The rationale for employing these measures is that they have been shown to be of utility for determining system changes in biologic signals.

From all the candidate measures (including signal energy, Approximate Entropy (ApEn), Cross-ApEn (C-ApEn), coherence, mutual information, short-term maximum Lyapunov (STLmax), pattern match regularity statistics (PMRS), Time-frequency distribution, and bi-spectrum index), we identify the measures that can be employed to distinguish the two groups of neonates, normal and abnormal. This can be accomplished, for each measure and each recording EEG channel, by the comparisons between normal and abnormal neonate groups utilizing ANOVA test. An overall significance (overall p-value, the smaller the p-value, the more significant the measure is) of the measure can be obtained by combining p-values across all EEG channels (Meta-analysis). An overall p-value less than 0.05 is considered as a significant measure. Groups of significant measures may vary with age.

In accordance with exemplary embodiments of the invention, a central program can be provided on the signal processing computer 106 for comparing all the output measures with individual pre-established optimal normal ranges (which for example can vary with age of the neonatal patient) to determine illness of the patient. The different measures or comparisons of the different measures with corresponding normal ranges, can be combined into a single composite wellness index. If the index is above or below a predetermined threshold, the signal processing computer can trigger an alarm to alert a health care professional that something is amiss with the patient. Seizures can be detected using a method weighting function (based on the "p-value" comparing with the baseline values) by considering all the linear and non-linear measures mentioned herein (e.g. signal energy, . . . bi-spectrum index, etc.) applied, for example, to the patient's EEG data. This process can involve two steps. First, detection of a seizure is declared from one measure if any of the recorded electrode sites above or below preset threshold values differ significantly from the interictal (baseline) values. Second, if there are certain numbers or combinations of measures that declare detections (or indicated likelihood of detection) at the same, a final decision that a seizure has been detected is established.

Figure 2:
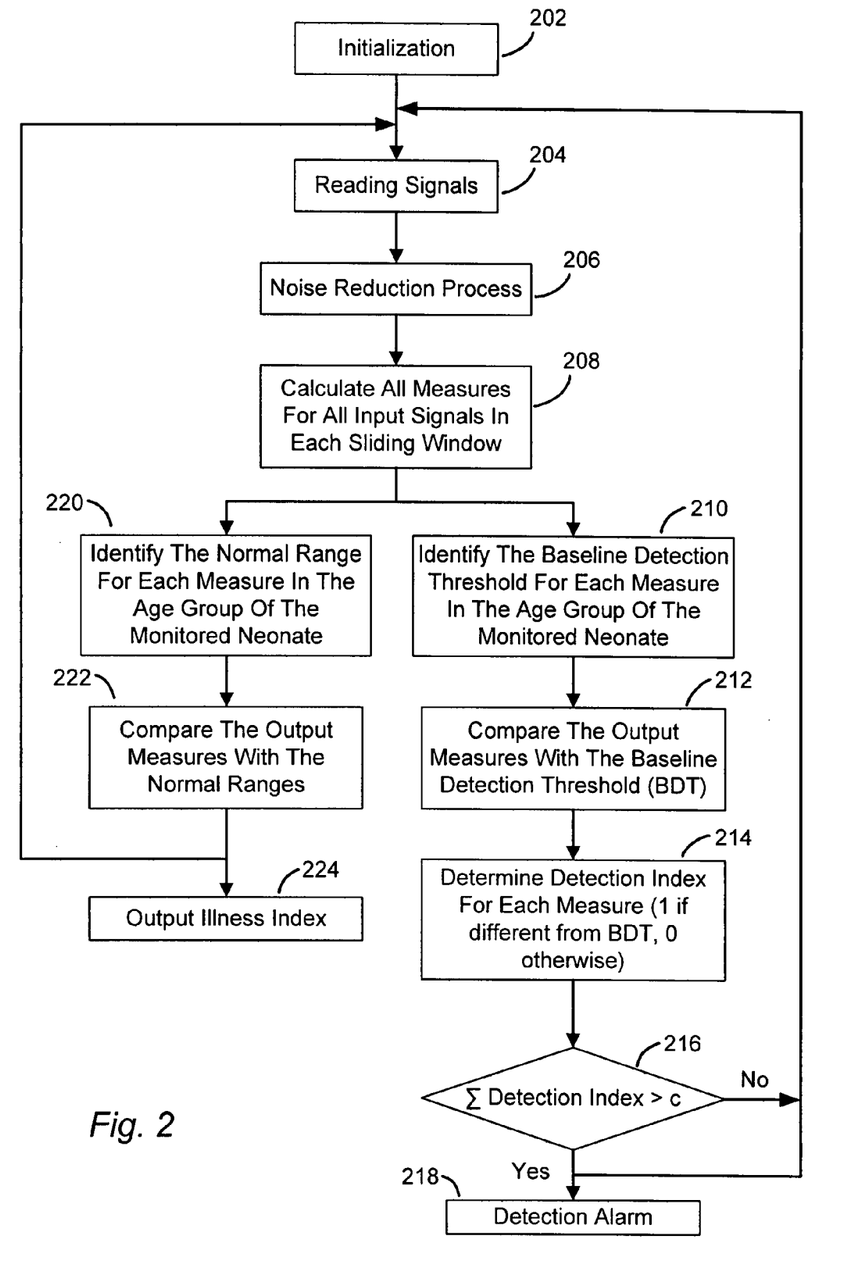
FIG. 2 illustrates an exemplary method.

FIG. 2 illustrates an exemplary method for processing captured patient data, that can be performed by the signal processing computer 106 and/or the signal acquisition machine 104. As shown in FIG. 2, in a first block 202, analysis program(s) are initialized. From block 202 control proceeds to block 204, where signals are read. From block 204 control proceeds to block 206, where noise reduction process(es) are applied to the signals. From block 206 control proceeds to block 208, measures (e.g. signal energy, . . . bi-spectrum index, etc.) are calculated for all input signals in each sliding window of signal data. From block 208, the calculated measures are provided to two different sub-processes for concurrent or independent processing, which begin with blocks 220 and 210 respectively.

In block 210, baseline detection thresholds are identified for each measure in the age group of the neonate patient being monitored. From block 210 control proceeds to block 212, where the calculated or output measures are compared against the identified baseline detection thresholds. From block 212, control proceeds to block 214, where a detection index is determined for each measure. For example, if a calculated measure exceeds or falls below a corresponding baseline threshold to indicate harm or danger to the patient, then the corresponding detection index is assigned a value of 1, otherwise the corresponding detection index is assigned a value of zero. From block 214, control proceeds to block 216, where a sum of the detection indices is compared against a threshold "c". If the sum exceeds the threshold, the control proceeds to block 218 where a detection alarm is triggered, for example to alert a health care professional that the patient requires attention. If in block 216 the sum does not exceeed the threshold, then control returns to block 204. In block 220, a normal range for each measure in the age group of the neonate patient being monitored, is identified. From block 220 control proceeds to block 222, where the output or calculated measures are compared against the normal ranges. A result of the comparison is output as a composite "illness index" in block 224, and control returns to block 204 so the cycle may repeat.

In exemplary embodiments of the present invention, a Brain Function Screen is provided for the assessment of brain maturity and function of a neonate. The Brain Function Screen can be implemented for example in the computer 106 and/or the machine 104, or can be separately implemented to perform in real time or in non-real time using stored data. The Brain Function Screen evaluates both cortical and subcortical systems of the brain. Evaluation of cortical maturity is accomplished by analysis of multi-channel EEG signal characteristics. An algorithm first creates parameter vector profiles over time for each recording channel. These parameter vectors include linear, nonlinear, univariate and bivariate quantitative measures derived from EEG signals, for example the measures described herein (ApEn, etc.). By applying the parameter vector on normal neonates in each conceptional age group, for each recording channel of the EEG signal, the probability distribution of each parameter can be approximated by estimating the probability density of each parameter.

In exemplary embodiments of the present invention, the Brain Function Screen further determines, for each channel of the EEG signal(s), a multidimensional joint probability distribution under normal conditions, for each conceptional age group, by combining all the individual probability distributions derived from each parameter in the parameter vector profiles. In addition, for each age group, the probability distribution of difference between two contralateral channels under normal conditions is defined. In addition, the Brain Function Screen can further define, for each age group, the joint probability distribution of differences between two contralateral channels under normal conditions by combining all the individual difference probability distribution derived from each parameter in the parameter vector profiles.

In exemplary embodiments of the present invention, the Brain Function Screen can achieve an overall evaluation of the cortical maturity of a neonate by at least one of the following four strategies. First, estimate the probability that a channel exhibits a parameter that is significantly different ($p<0.05$) from the mean of the normal neonates. Second, estimate the probability that a channel exhibits the parameter vector that is far away from the joint probability distribution of normal neonates. Third, estimate the probability that a pair of contralateral channels exhibits significant difference ($p<0.05$) in a parameter. Fourth, estimate the probability that a pair of contralateral channels exhibits the parameter vector that is far away from the joint probability distribution of normal neonates.

In exemplary embodiments of the present invention, the Brain Function Screen evaluates subcortical maturity by analyzing evoke potential signals including brainstem auditory evoke, somatosensory, visual responses, etc. The algorithm will first determine the latency between the stimulus and evoked responses by automatically detecting the peak-to-peak intervals in the response profiles.

The latency of each response in each conceptional age group will form a latency vector. By generating latency vector profiles in a group of normal neonates for each conceptional age group, the Brain Function Screen can estimate probability density distribution for each response.

In exemplary embodiments of the present invention, the Brain Function Screen further provides a multidimensional joint probability distribution under normal conditions, for each conceptional age group, by combining all the individual probability distributions derived from each response in the latency vector profiles.

In exemplary embodiments of the present invention, the Brain Function Screen further defines, for each conceptional age group and each response, a probability distribution of latency difference between left and right under normal condition. These individual probability distributions can be combined to define, for each conceptional age group, a joint probability distribution of latency difference between left and right under normal conditions In exemplary embodiments of the present invention, the Brain Function Screen can achieve an overall evaluation of the subcortical maturity of a neonate by at least one of the following strategies four strategies. First, estimate the significance (p-value) of how the latency of a response is different from the mean of the normal neonates. The overall p-value can be obtained by applying Meta analysis. Second, estimate the significance (p-value) of how the latency vector is far away from the joint distribution of the normal neonates. Third, estimate the significance of how the left-right latency difference, for each response, is different from the mean of the normal neonates. The overall p-value can be obtained by applying Meta analysis. Fourth, estimate the significance (p-value) of how far away the left-right latency difference vector is from the joint distribution of the normal neonates.

The Brain Function Screen combine, or can be a combination of, results from the cortical and subcortical system evaluations.

In exemplary embodiments of the present invention, and as described elsewhere herein, a Neonatal Brain Function Monitoring System is provided for monitoring the brain function of a neonate in real time. The Neonatal Brain Function Monitoring System can be implemented for example in the computer 106 and/or the machine 104, or can be separately implemented.

The Neonatal Brain Function Monitoring System provides a quantitative tool for monitoring the brain function of a neonate in real time. An objective of Neonatal Brain Function Monitoring System is to apply quantitative analyses for the detection of state changes in a neonatal brain. These state changes include epileptic seizures and other abnormal brain activities. In addition, the Neonatal Brain Function Monitoring System performs analysis of multi-channel EEG time series and evoked potential responses. In particular, for the EEG analysis the Neonatal Brain Function Monitoring System first generates, for each recording channel, multiple quantitative profiles including linear, nonlinear, univariate and bivariate measures, for example the measures described herein (ApEn, etc.). For the detection of a state change, the Neonatal Brain Function Monitoring System of the present invention employs a "voting scheme" method by considering all the quantitative measures. This scheme includes two steps. First, a detection is declared from one measure if any of the recorded channels rises/falls above/below the preset threshold values derived from normal state periods. Second, if there are certain numbers of measures that declare detections of state changes at the same time window, the final decision for detecting a state change will be established.

In accordance with exemplary embodiments, for the evoked potential analysis, the Neonatal Brain Function Monitoring System first generates the latency profiles between the stimulus and evoked responses (auditory, somatosensory, visual responses, etc). For the detection of a state change, the Neonatal Brain Function Monitoring System declares detection if any of the latency profiles rises/falls above/below the preset threshold values derived from normal state periods or intervals. In addition, the Neonatal Brain Function Monitoring System declares detection of an abnormal state change if either one of the EEG detection or the evoked potential detection is declared.

Returning now to further discussion of the illness index mentioned above and referenced, for example, in block 224 of FIG. 2, different methods can be used to establish or calculate the illness index.

In a first method for establishing or calculating the illness index, for each of the measures (e.g. signal energy, . . . bispectrum index and so forth) a normal confidence range is established that varies with age or age group of the child, for each of the recording EEG channels. These ranges are obtained from a (sample) group of normal neonates. For each test or sample neonate, a segment (normally 30-60 minutes) of multi-channel EEG is recorded and time profiles of the measures (corresponding to the age of the neonate) are generated. The mean value (over a recording segment) of each measure from each channel is compared with the corresponding normal confidence range. Significance (p-value) of each measure for that recording segment is estimated by considering all channels.

One possible scheme is to estimate the p-value by calculating the percentage of channels that significantly differ from the normal mean value (that is, the value falls outside the normal confidence range). If this is employed, binomial distribution may be utilized to obtain the p-value. Another possible scheme to estimate the significance of each measure is simply considering the most significant EEG channel that is most significantly different from the normal mean value (that is, channel with the minimum p-value). After estimating significance of all measures, an illness index of the test neonate during the recording segment is represented by the overall significance (p-value) over all measures. This index can be obtained by combining p-values across all considered measures (Meta analysis). The illness index can be an output that varies over time with different recording segments. In an exemplary embodiment, smaller illness indices suggest that the brain activities of the test neonate are more abnormal.

In a second method, for each age group, an overall normal confidence range is established from a group of normal neonates. This confidence range is based on the weighted function from each of the considered measures, where the weight of each measure may be equal to (1−p-value), and the p-value is the significance of the measure for distinguishing normal from abnormal neonate groups described above. Specifically, the weighted function can be formulated as:

For neonate i:

$$Neo_i = \sum_{j=1}^{J} w_j X_{ij}$$

where $w_j$ is the weight for measure j, and $X_{ij}$ is the mean output of measure j over all channels obtained from normal neonate i.

After obtaining {Neo1, Neo2, . . . , NeoI} from 1 normal neonates, a normal confidence range can be constructed by estimating their mean value and standard deviation.

For each test neonate, a segment (normally 30~60 minutes, for example) of multi-channel EEG is recorded and all considered measures are calculated. After the recording, a value of the weighted function is calculated and it is compared with the normal confidence range for the corresponding age group. After estimating significance of the weighed function value, an illness index of the test neonate is represented by the significance (p-value) of the value. The illness index can be an output over time with different recording segments. Smaller illness indices suggest that the brain activities of the test neonate are more abnormal.

In a third method, measure vector profiles over time are first created for each recording channel. By applying the measure vector on normal neonates in each age group, for each channel, the probability distribution of each measure can be approximated by estimating the probability density of each measure. Another possibility is to estimate a multi-dimensional joint probability distribution, for each recording EEG channel, by combining all the individual probability distribution derived from each parameter in the measure vector profiles.

The illness index for each test neonate can be an output of the probability that a channel exhibits at least a measure whose probability distribution is significantly different ($p<0.05$) from that obtained from the normal neonates. The illness index for each test neonate can also be an output of the probability that a channel exhibits the parameter vector whose joint probability distribution is significantly different ($p<0.05$) from that obtained from the normal neonates.

In general, the illness index (created for example by one of the methods described above or by a different method) may also be used for the real-time detection or prediction of an abnormal brain activity during a monitoring procedure, for example a seizure. In this application, the illness index is calculated for each sliding time window of data. The window length may, for example, be equal to 10 minutes, and may shift 10 seconds each time. The detection/prediction threshold (critical value) may be determined by estimating the mean illness index during a baseline period. The illness index may be derived from any of the three "illness index" methods described above.

To establish a normal range for each of the measures (e.g. the measures mentioned herein such as signal energy, . . . bi-spectrum index, and so forth) with respect to a patient age group, the mean value and standard deviation for each identified measure can be initially estimated for a block of data from neonates in that age group who did not have seizures. For example, the data can comprise twelve 1-hour recordings (e.g. EEG recordings). Age is important because natural brain function in young children and particularly neonates develops rapidly, so that baseline or normal brain function is different for different age groups. Next, a new set of recordings from each of the two categories (those who experienced seizures, and those who did not) of newborns are used to train or help define an optimal normal range (e.g. mean plus or minus x*STD) for each identified measure in each age group by creating a receiver operating characteristics (ROC) curve from the training sensitivity and specificity results. For this purpose, the following definitions are employed.

Positive: Measures fall outside the normal range.

Negative: Measures fall within the normal range.

True positive: Measures successfully identify category of newborn with seizures.

True negative: Measures successfully identify category of newborn without seizures.

False positive: Measure incorrectly identify category of newborn with seizures.

False negative: Measure incorrectly identify category of newborn without seizures.

The final step is to validate (e.g. statistically) the established optimal normal ranges by testing them in a new testing data set including both categories of newborns and all studied age groups.

The neonate seizure detection method can be evaluated by the sensitivity and false detection rate per hour. For statistical validation of the neonate seizure detection method, we can first create ROC curves in the training data sets to optimize the thresholds for each age group studied. Optimal threshold results can then be employed to a testing data set, which will include all age groups in order to evaluate the performance of the seizure detection method. Consistent with this purpose, the following definitions are employed.

Seizure onset: An electrographic seizure is defined as the presence of abnormal repetitive discharges with a clear onset and typical evolution in space and time, lasting at least 10 seconds.

Detection: A unitary event defined to exist when the value of the measured dependent variable remains beyond a threshold value for a specific period of time.

True detection: The detection is included in a seizure ictal period.

False detection: The detection is not included in any seizure ictal period.

Sensitivity: Number of seizures detected divided by the total number of seizures.

False detection rate (per hour): Total number of false detections divided by total number of recording hours.

With respect to the different measures, we employed energy because it is a first level measure of a system behavior and necessary to the understanding of system behavior.

We selected STLmax because we have found it useful for identifying pre-seizure changes in adults with temporal lobe epilepsy. Previous studies by our group have shown that measures of the spatiotemporal dynamical properties of the EEG demonstrate patterns that correspond to specific clinical states.

We selected coherence because it is well understood and completely characterized. Coherence is a measure used to determine the degree of linear similarity between two signals. Coherence can be applied to the human EEG in order to determine the relationship between signals for determining seizure propagation delay.

The mutual information statistic provides a measure of the relationships between two variables that do not require Gaussian probability distributions. In exemplary embodiments, the mutual information statistic provides an index of the interdependencies of EEG signals that measures both linear and non-linear interactions of the time-series.

Approximate entropy (ApEn) is univariate and cross-ApEn, are bivariate measures derived from the theory of nonlinear statistics. ApEn is a regularity statistic, which quantifies the complexity of a time series. Cross-ApEn quantifies the asynchrony or conditional irregularity between two standardized time series. Both ApEn and cross-ApEn measures can be applied on short data segments, and are less sensitive to non-stationarity and noise, two essential attributes of biological signals.

By way of further background, in very general terms an epileptic system is a spatially distributed system of groups of neurons located in the deep regions of the brain, which cooperate to control the onset, propagation, and arrest of epileptic seizures. Quantifying such a system requires knowledge of the system, an observable and reproducible objective measure that can be modeled, and expertise of the analytical methods to be employed to model the observable changes. Requisite to these challenges for the proposed study are an adequate knowledge of newborn seizure phenomenology, ability to acquire, collect, and process sufficient quantity of EEG data, and mastery of the analytical methods to be employed to analyze newborn EEG signals. The University of Florida Comprehensive Pediatric Epilepsy Program, the University of Florida Neonatal Division, and the Biomedical Research Partnership group have performed extensive work on the study of epilepsy. This section contains preliminary data of some of our recent work. Methods and experimental design are further outlined in this document.

Three patients from each category of newborn were studied, to identify specific differences in brain electrical activity through measurements of signal energy, ApEn, cross-ApEn, coherence, mutual information, and STLmax of continuous scalp EEGs recorded from a) newborns with seizures and b) newborns without seizures, matched for conceptional age and medical condition. In addition, normal ranges of measures were established to distinguish the category of newborns with seizures, from the category of newborns without seizures, by defining the optimum confidence interval as a function of conceptional age. The identified specific differences in brain activity between newborns with and without seizures (including the established normal ranges) were then used to detect seizures in neonatal children. In addition, threshold measures were established or developed to distinguish the interictal state from the seizure period by defining the optimal confidence interval for each measure as a function of conceptional age.

In particular, conceptional age (CA) and 5 minute Apgar score for each newborn were provided/recorded, and an EEG from an 11-electrode montage based on the 10-20 international system was recorded (12-bit A/D conversion, 256 Hz sampling, 0.1-70 HZ signal bandwidth) and stored in digital form along with a time synchronized video signal of the patient. All recordings were obtained with continuous supervision by a licensed EEG technician. All newborn EEGs for each category of patient were scored by a certified electroencephalographer for wake and sleep states using the criteria established by Stockard-Pope et al. and Scher. Seizure type and onset/offset seizure times were documented.

The following linear and nonlinear univariate and bivariate measures were used for the preliminary studies: signal energy, approximate energy (ApEn), cross-ApEn, coherence, mutual information, and short-term maximum Lyapunov exponent (STLmax or $STL_{max}$). Each measure was applied to continuous 0.5-1 hour 11-channel bipolar EEG recordings iteratively at 4-second epochs (sampling frequency 256 HZ). Preliminary results were obtained from archived data collected from newborn patients that had been cared for in the newborn intensive care unit at Shands/University of Florida Health Center, Gainesville, Fla.

Signal Energy

We tested both conventional energy and Teager energy for their utility in differentiating epileptic and physiologic states, and detecting recorded seizures in full-term newborns/neonates. EEG recordings of normal physiologic and seizure intervals were divided into non-overlapping four-second segments (1024 points). Briefly, the results showed that Teager energy greatly increased at the time of the recorded seizure. We did not see significant increases in Teager energy during interictal seizure periods. Teager energy remained for the most part constant in normal newborn EEGs, although we did see minor increases in energy, which we suspect, might represent transitions from quiet to active sleep or an arousal. No change in conventional energy was noted at the time of seizure. Likewise, we did not see changes in signal energy during the immediate post-ictal period. In this limited sample, we did not identify false seizure detections with either method. These preliminary results suggest that Teager energy may be a superior method to conventional energy for detecting neonatal seizures from surface recorded EEGs.

Approximate Entropy

Our preliminary results suggest that full-term infants with seizures and without seizures are significantly different with respect to their ApEn values. Newborns with seizures showed greater ApEn values during the interictal period, while newborns without seizures showed significantly lower ApEn values. ApEn values reached their lowest value during seizures, suggesting that ApEn may be a useful method for detecting seizure periods.

Cross-ApEn

Our results suggested that each category of newborn is significantly different with respect to their cross-ApEn values over pairs of electrode sites. Newborns with seizures show greater cross-ApEn values relative to newborns without seizures. Furthermore, seizure periods corresponded to lower cross-ApEn values, suggesting that this measure may serve to separate newborns with seizures from those without seizures, as well as detecting seizure intervals.

Coherence

Results failed to distinguish any significant differences between the two categories of newborns. However, coherence values were observed to significantly change at seizure times, especially at frequencies between 10-35 Hz.

Mutual Information

Our preliminary results did not show significant differences with respect to the two categories of newborns using the mutual information measure. Likewise, this limited sample size did not allow us to detect seizure periods using this method. A possible explanation for the lack of significant differences between the two groups may be explained in part by this measure's sensitivity to noise. Thus, better results may be possible following preprocessing of the EEG data.

Maximum Short-Term Lyapunov Exponent

STLmax values for each category of newborn showed significant differences between two groups. Each newborn with seizures showed relative lower STLmax values during the entire recording period. In addition, STLmax values decrease during seizure intervals. Relative STLmax values were persistently higher in the newborns that did not exhibit seizures, and whose EEGs were scored as being normal.

EXEMPLARY DESIGN AND METHODS

Patients

Use can be made of archived data collected from newborn patients that have been characterized in the newborn intensive care unit at Shands/University of Florida Health Center, Gainesville, Fla. The scalp EEG data archived at Shands/University of Florida Health Center contains combined digital continuous video-EEG recordings, and archived data of all seizures recorded from all newborns evaluated for seizures and brain electrical activity. Interictal and seizure recordings of one-hour duration are available in this archive. At the University of Florida Health Science Center, we currently have more that 700 archived 1-hour neonatal recordings with two-hundred fifty 1-hour recordings demonstrating at least one clearly defined seizure. It is common practice in our institution to perform serial EEG recording in neonates with documented EEG seizures as we attempt to document the therapeutic effect of anticonvulsant treatments.

Analysis to identify specific differences in brain electrical activity between newborns with and without seizures can be conducted on random data sets recorded from full-term (conceptional age 38-42 weeks) infants with and without seizures from each of the following age groups: (1) 38-39 weeks, (2) 39-40 weeks, (3) 40-41 weeks, and (4) 41-42 weeks. Analysis can be performed to identify the most robust measures that will distinguish the two categories of newborns (with and without seizures) in each of the four age groups, and establish the confident quantitative normal range from the identified measures in order to detect newborns that might be vulnerable to seizures. The category of newborns in each age group can be used to define the optimal normal range. Patient data such as the age of the newborn, 5-minute Apgar score, birth weight, sex, cardiopulmonary resuscitation, vital signs, oxygenation, serum electrolytes, medications, anticonvulsant dose, anticonvulsant serum trough levels, and brain neuroimaging results can be documented for each category of newborn. Also, information such as electrode position, patient state, as well as the suspected known location and seizure onset time, can be scored by two certified clinical neurophysiologists in order to test the algorithms. The following definition of neonatal seizure can be used: An electrographic seizure is defined as the presence of abnormal repetitive discharges with a clear onset and typical evolution in space and time, lasting at least 10 seconds.

Data Acquisition

Newborns can be monitored continuously using a commercial EEG acquisition and storage system, for example the Nicolet/BSMI 6000, of Madison, Wis. An 11-electrode montage based on the 10-20 international systems can be recorded (12-bit A/D conversion, 256 Hz sampling, 0.1-70 HZ signal bandwidth) and stored in digital form along with a time synchronized video signal of the patient. All recordings can be obtained with continuous supervision by a licensed EEG technician. All newborn EEGs for each category of patient can be scored by two certified clinical neurophysiologists for wake and sleep states using the criteria established by Stockard-Pope, et al. and Scher. A dedicated computer on the network can be employed to continuously archive data to high capacity DVD (Digital Versatile Disc). This dedicated computer can also be employed to perform real-time processing of recorded EEGs. A second Nicolet/BSMI machine can be used for offline reformatting and reviewing of EEGs. The data can be analyzed on multiple networked computers, for example Pentium 4 processor based networked computers, and multiple signal analysis software programs can be employed in this project for quantitative EEG analyses.

Quantitative EEG Measures

As previously mentioned, exemplary methods can be used to evaluate the EEG measurements, including for example signal energy, approximate energy (ApEn), crossApEn, coherence, mutual information, short-term maximum Lyapunov exponent (STLmax), pattern-match ApEn and/or pattern-match regularity statistics, TFDs, and bi-spectrum index. All methods can be performed iteratively at periodic intervals, for example at every 4-second epoch (or any other interval), on bipolar scalp EEGs recordings from each category of newborn. It can be important to select in advance, the appropriate electrode sites that give the most robust result for each measure. Unlike adult partial focal epilepsy where the optimal sites have been shown to reside near the seizure focus, in the newborn, seizures are often multifocal and can alternate hemispheres within a given seizure. Therefore, in an exemplary embodiment, all electrode sites comprising the neonatal montage outlined earlier herein, are selected.

Signal Energy

The use of this measure is based in part on the reported utility of signal power (signal energy) to predict seizures and detect physiological sleep states in patients with temporal lobe epilepsy, which observations suggest that EEG signal energy may be greater during seizure periods relative to interictal and postictal states. Average signal energy can be calculated with both the conventional measure of energy and Teager algorithm. The conventional measure of signal energy considers contributions from all frequencies of a signal in equal fashion. Teager energy weighs contributions of differential frequencies in a non-uniform fashion, emphasizing higher frequencies by square law weighing. Teager energy has been found to be useful to detect seizures in patients with temporal lobe energy. This method is attractive because it is adaptable to time-varying signals, simple to execute, and physically discerning. Accumulated energy methods can also be executed on all data sets, to help identify pre-seizure and seizure periods in patients with temporal lobe epilepsy. In an exemplary embodiment, the average energy in each 4-second window of EEG signal is estimated before employing the accumulated energy to data sets.

Approximate Entropy

In an exemplary embodiment, two input parameters, m and r, are specified in order to calculate ApEn. ApEn measures the likelihood that sets of patterns remain in close proximity (r) for m observations. It is a relative measure of process regularity, which can show significant variation in its absolute numerical value, as background and noise characteristics of the EEG signal vary over time. In order to compensate for increasing processing noise, data sets from a fixed experimental setting (m and r) can be compared.

Cross-ApEn

Cross ApEn quantifies the asynchrony (conditional irregularity) between two standardized time-series. We can apply known algorithms, for example the algorithms described by Pincus (1991), to each data set for each category of newborn. Cross-ApEn can be employed for each (e.g., 4-second) non-overlapping window (comprising, e.g., 1024 points) for each pair of EEG electrodes.

Coherence

Coherence can be used to measure the degree of linear similarity between two signals. In an exemplary embodiment, coherence is applied to each (e.g., 4-second) non-overlapping window (comprising, e.g., 1024 points) of EEG signal for each category of newborn. We can apply known tests, e.g. the tests described by Zaveri, et al. (1999). In an exemplary embodiment, we test coherence with caution, keeping in mind the effect of EEG non-stationarity on estimates.

Mutual Information

In an exemplary embodiment, mutual information is applied or employed to EEG data sets for each category of newborn in order to measure the statistical dependency between electrode pairs. Average mutual information is calculated using signals from electrode pairs in non-overlapping epochs or time intervals, e.g. epochs having 1024 points and a duration of 4 seconds. The average mutual information for individual electrode pairs and the average over all unique electrode pairs is evaluated. In an exemplary embodiment, embedding dimensions are explored in order to preserve the temporal dynamics of the signal, beginning for example with an embedding dimension $m=3$.

Maximum Short-Term Lyapunov Exponent (STLmax)

STLmax estimates the stability of a dynamical system. Low STLmax values suggest a more ordered system. In an exemplary embodiment, for each recording the STLmax algorithm is applied for each non-overlapping (e.g. 4-second) window sequentially. The degree of convergence among electrode pairs can also be evaluated.

Statistical Analysis Methodology

Each of the measures described above can be applied to each 1-hour EEG recording over time from newborns in each category, and for each age group. In order to account for variations within each category of newborns, for each of the measures, Nested ANOVA test can be employed to test the category effect. The measures that show the significant effect ($p<0.05$) in the test can be identified as the most robust measures to distinguish the two categories of newborns.

In an exemplary embodiment, requisite to 90% of power and 95% confidence level to detect the effect within 1 standard deviation of the overall variation each age group, at least 12 newborns in each category are required. Thus, a total of 96 newborns of 1-hour EEG recordings can be acquired to achieve the desired power and the confidence level of the test.

In an exemplary embodiment, after identifying the optimal measures to distinguish the two categories of newborns (seizure and non-seizure), the next step is to establish the normal range for each of the identified measures in each age group to establish the likelihood of presenting seizures. For each age group, we can initially estimate the mean value and standard deviation for each identified measure from the twelve 1-hour recordings in the category of newborns without seizures. Second, we can use a new set of recordings from each of the two categories of newborns to train the optimal normal range (mean ±STD) for each identified measure in each age group by a creating receiver operating characteristics (ROC) curve from the training sensitivity and specificity results. For this purpose, the following definitions are employed.

Positive: Measures fall outside the normal range.
Negative: Measures fall within the normal range.
True positive: Measures successfully identify category of newborn with seizures.
True negative: Measures successfully identify category of newborn without seizures.
False positive: Measure incorrectly identify category of newborn with seizures.
False negative: Measure incorrectly identify category of newborn without seizures.

The final step is to validate the established optimal normal ranges by testing them in a new testing data set including both categories of newborns and all four age groups. The table below indicates exemplary accuracy and confidence levels corresponding to different sample sizes:

TABLE 1

Sample (newborns) size & corresponding Confidence and Accuracy

| | | Confidence Level | | |
|---|---|---|---|---|
| | | 90% | 95% | 99% |
| Accuracy | ±5% | 1084 | 1540 | 2656 |
| | ±10% | 272 | 388 | 664 |
| | ±15% | 124 | 172 | 296 |

DEFINITIONS

Seizure onset: An electrographic seizure is defined as the presence of abnormal repetitive discharges with a clear onset and typical evolution in space and time, lasting at least 10 seconds.

Detection: A unitary event defined to exist when the value of the measured dependent variable remains beyond a threshold value for a specific period of time.

True detection: The detection is included in a seizure ictal period.

False detection: The detection is not included in any seizure ictal period.

Sensitivity: Number of seizures detected divided by the total number of seizures.

False detection rate (per hour): Total number of false detections divided by total number of recording hours.

In an exemplary embodiment, a detection method can be evaluated by the sensitivity and false detection rate per hour.

EXPERIMENTAL METHODS

For the category of newborns with seizures, evaluate data (including continuous scalp EEGs) using measurement criteria such as those mentioned herein (e.g. signal energy, ApEn, cross-ApEn, coherence, mutual information, STLmax, pattern-match ApEn and/or pattern-match regularity statistics, TFDs, and bi-spectrum index) to identify specific differences in brain electrical activity, and establish a normal range of measures that distinguish newborns or neonates with and without seizures and then use this information to detect seizures, e.g. of newborns or neonates being monitored.

In addition, establish threshold measures that distinguish the interictal state from the seizure period by defining the optimal confidence interval for each measure as a function of conceptional age.

In an exemplary embodiment, seizures can be detected via a "voting scheme" method by considering all the linear and nonlinear measures mentioned herein (e.g., signal energy, ApEn, cross-ApEn, coherence, mutual information, STLmax, and so forth). Briefly, this scheme entails two steps. First, detection is declared from one measure if any of the recorded electrode sites above/below the preset threshold values varies significantly from the interictal period (baseline) values. Second, if there are certain numbers of measures that declare detections at the same time, a final decision for detecting a seizure can be established.

Statistical Analysis

In an exemplary embodiment, a seizure detection method can be statistically validated by first creating ROC (Receiver Operating Characteristic) curves in the training data sets to optimize the thresholds in the proposed method for each age group studied. Optimal threshold results will then be employed to a testing data set, which will include all age groups in order to evaluate the performance of the proposed seizure detection method.

The methods, logics, techniques and pseudocode sequences described herein can be implemented in a variety of programming styles (for example Structured Programming, Object-Oriented Programming, and so forth) and in a variety of different programming languages (for example Java, C, C++, C#, Pascal, Ada, and so forth). In addition, those skilled in the art will appreciate that the elements and methods or processes described herein can be implemented using a microprocessor, computer, or any other computing device, and can be implemented in hardware and/or software, in a single physical location or in distributed fashion among various locations or host computing platforms. Agents can be implemented in hardware and/or software or computer program(s) at any desired or appropriate location. Those skilled in the art will also appreciate that software or computer program(s) can be stored on a machine-readable medium, wherein the software or computer program(s) includes instructions for causing a computing device such as a computer, computer system, microprocessor, or other computing device, to perform the methods or processes.

A machine readable medium can include software or a computer program or programs for causing a computing device to perform the methods and/or techniques described herein.

It will also be appreciated by those skilled in the art that the present invention can be embodied in other specific forms without departing from the spirit or essential characteristics thereof, and that the invention is not limited to the specific embodiments described herein. The presently disclosed embodiments are therefore considered in all respects to be illustrative and not restrictive. The scope of the invention is indicated by the appended claims rather than the foregoing description, and all changes that come within the meaning and range and equivalents thereof are intended to be embraced therein.

What is claimed is:

1. A method for monitoring neonate brain function, comprising:

processing electroencephalographic data of the neonate to calculate a plurality of measures, at least one measure including a non-linear measure, wherein the at least one measure is selected from a group consisting of signal energy, approximate entropy (ApEn), short-term maximum Lyapunov exponent (STLmax), cross-ApEn, coherence, mutual information, pattern-match ApEn, pattern-match regularity statistics, and time-frequency distributions;

comparing the calculated at least one measure against at least one baseline threshold, wherein the at least one baseline threshold corresponds to a neonate age range;

outputting a result of the comparison;

generating an illness index of the neonate based on the comparison result; and displaying the illness index, wherein the illness index is a weighted combination of comparison results corresponding to the plurality of measures.

2. The method of claim 1, comprising displaying the result, wherein the result indicates health of the neonate.

3. The method of claim 1, wherein the result indicates whether the neonate's brain is functioning normally.

4. The method of claim 1, wherein the generating comprises:

comparing a mean value of each of the plurality of measures for each of multiple channels of the electroencephalographic data over a time interval, against a corresponding normal confidence range;

estimating a significance of each of the measures; and based on the mean values and corresponding significances of the measures, combining the measures to form the illness index.

5. The method of claim 4, wherein the normal confidence range varies with age or age group of the neonate.

6. The method of claim 1, wherein the generating comprises:

calculating a value of a weighted function of the plurality of measures; and estimating a significance of the calculated value based on a comparison of the value with an overall normal confidence range, wherein the estimated significance forms the illness index.

7. The method of claim 1, wherein the illness index corresponds to a probability that one of the plurality of measures for a channel of the encephalographic data has a probability distribution that is significantly different from a corresponding measure for a group of normal neonates.

8. The method of claim 7, wherein the probability distribution is significantly different when $p<0.05$.

9. The method of claim 1, comprising triggering an alarm when the illness index crosses a predetermined threshold.

10. A system for monitoring neonate brain function, comprising:

a computing device for processing electroencephalographic data of the neonate to calculate a plurality of measures, at least one measure including a non-linear measure, and for comparing the calculated at least one measure against at least one baseline threshold, wherein the at least one baseline threshold corresponds to a neonate age range; and a display for displaying a result of the comparison, wherein the at least one measure is selected from a group consisting of signal energy, approximate entropy (ApEn), short-term maximum Lyapunov exponent (STLmax), cross-ApEn, coherence, mutual information, pattern-match ApEn, pattern-match regularity statistics, and time-frequency distributions, wherein the computing device is arranged to generate an illness index of the neonate based on the comparison result and display the illness index on the display, and wherein the illness index is a weighted combination of comparison results corresponding to the plurality of measures.

11. The system of claim 10, wherein the displayed result indicates whether the neonate's brain is functioning normally.

12. The system of claim 11, comprising an alarm system that is triggered when the neonate's brain is functioning abnormally.

13. The system of claim 10, wherein the illness index is generated by:

comparing a mean value of each of the plurality of measures for each of multiple channels of the electroencephalographic data over a time interval, against a corresponding normal confidence range;

estimating a significance of each of the measures; and based on the mean values and corresponding significances of the measures, combining the measures to form the illness index.

14. The system of claim 13, wherein the normal confidence range varies with age or age group of the neonate.

15. The system of claim 10, wherein the illness index is generated by:

calculating a value of a weighted function of the plurality of measures; and estimating a significance of the calculated value based on a comparison of the value with an overall normal confidence range;

wherein the estimated significance forms the illness index.

16. The system of claim 10, wherein the illness index corresponds to a probability that one of the plurality of measures for a channel of the encephalographic data has a probability distribution that is significantly different from a corresponding measure for a group of normal neonates, wherein the probability distribution is significantly different when $p<0.05$.

* * * * *